United States Patent [19]

Gerig et al.

[11] Patent Number: 5,446,548
[45] Date of Patent: Aug. 29, 1995

[54] PATIENT POSITIONING AND MONITORING SYSTEM

[75] Inventors: Lee H. Gerig, Almonte; Sabry F. El-Hakim, Ottawa, both of Canada

[73] Assignee: Siemens Medical Systems, Inc., Iselin, N.J.

[21] Appl. No.: 134,362

[22] Filed: Oct. 8, 1993

[51] Int. Cl.⁶ .............................................. G01B 11/03
[52] U.S. Cl. ..................... 356/375; 250/462.1; 128/653.1; 378/69; 378/205; 364/413.26
[58] Field of Search .................. 356/373, 375; 250/458.1, 462.1, 491.1; 378/20, 65, 68, 69, 96–97, 108, 205, 206; 359/516, 517, 519; 364/413.26; 128/653.1; 606/130; 601/2; 607/88

[56] References Cited

U.S. PATENT DOCUMENTS

| | | | |
|---|---|---|---|
| 3,629,594 | 12/1971 | Sandberg | 378/206 |
| 3,783,251 | 1/1974 | Pavkovich | 378/196 |
| 3,861,807 | 1/1975 | Lescrenier | 356/152 |
| 3,906,233 | 9/1975 | Vogel | 378/65 |
| 4,262,306 | 4/1981 | Renner | 358/93 |
| 4,791,934 | 12/1988 | Brunnett | 128/653 |
| 5,014,290 | 5/1991 | Moore et al. | 378/145 |
| 5,080,100 | 1/1992 | Trotel | 128/653.1 |
| 5,107,839 | 4/1992 | Houdek et al. | 128/653.1 |
| 5,138,647 | 8/1992 | Nguyen et al. | 378/189 |
| 5,193,106 | 3/1993 | DeSena | 378/163 |
| 5,207,223 | 5/1993 | Adler | 606/130 |
| 5,233,990 | 8/1993 | Barnea | 128/653.1 |
| 5,279,309 | 1/1994 | Taylor et al. | 128/782 |
| 5,295,483 | 3/1994 | Nowacki et al. | 601/2 |
| 5,300,783 | 4/1994 | Spencer et al. | 250/462.1 |
| 5,306,271 | 4/1994 | Zinreich et al. | 378/20 |
| 5,315,630 | 5/1994 | Sturm et al. | 378/65 |

FOREIGN PATENT DOCUMENTS

| | | | |
|---|---|---|---|
| 253017 | 1/1988 | European Pat. Off. | 356/375 |
| 0560331 | 9/1993 | European Pat. Off. | |
| 4120074 | 1/1992 | Germany | 606/130 |
| 246611 | 10/1988 | Japan | 356/375 |

OTHER PUBLICATIONS

Abstract entitled "Optical Measurements of Patient Position and Movement in Two Alternative Head Holder Systems", Menke et al., published in the International Journal of Radiation, Oncology, Biology and Physics, vol. 24, Supplement 1, pp. 189–190, Proceedings of the 34th Annual ASTRO Meeting (1992).

Primary Examiner—F. L. Evans
Attorney, Agent, or Firm—Lawrence C. Edelman

[57] ABSTRACT

The present invention is a remote sensing system for real time monitoring of patient position which can report variations in patient setup from day to day as well as motion during individual treatments. In particular, an embodiment of the present invention includes: (a) a source of radiation for applying radiation to a patient; (b) targets affixed to the patient for reflecting radiation impinging thereon; (c) two cameras and a computer for detecting the reflected radiation and for determining the current position of the targets in three-dimensional space; (d) a data store for storing the position of the targets; (e) the computer also serving to compare the current position of the targets with positions stored in the data store; and (f) a display for displaying indicators whenever differences between the current position and the stored position exceed tolerances stored in the data store.

41 Claims, 3 Drawing Sheets

5,446,548

PATIENT POSITIONING AND MONITORING SYSTEM

TECHNICAL FIELD OF THE INVENTION

The present invention relates to methods and apparatus for patient positioning and for verifying treatment fields in the delivery of radiation therapy.

BACKGROUND OF THE INVENTION

Accurate placement and verification of treatment fields remain as principal problems in the delivery of radiation therapy. Measurements of patient setup and field positioning errors have been reported by many authors. For example, many published reports document positioning errors having mean deviations of the order of 5 to 8 mm, wherein a significant percentage of positioning errors occur in excess of 15 mm. One example of such reports can be found in an article entitled "Quality Assurance in Radiation Therapy: Physics Efforts" by Svensson, G. K., Int. J. Rad. Onc. Biol. Phys., Vol. 10, Sup 1, 23–29, 1983.

As is well known, such positioning errors lead to a decrease in Tumor Control Probability (TCP) which can be as large as 20 percent (20%). One example of such results can be found in an article entitled "Uncertainty Analysis of Field Placement Error Measurements Using Digital Portal and Simulation Image Correlations" by McParland, B. J., Med. Phys., 20(3), 679–685, May/June 1993.

Many groups have attempted to address this issue by using "port films" or real time portal imaging technology. One example of such attempts is described in an article entitled "Automatic On-line Inspection of Patient Set-up in Radiation Therapy Using Digital Portal Images" by Gilhuijs, K. G. A. and van Herk, M., Med. Phys., 20(3), May/June 1993. See also U.S. Pat. No. 5,138,647 entitled "Portal Imaging Device" issued Aug. 11, 1992 to Nguyen, J. and Yu, C. X. and assigned to Siemens Medical Laboratories, Inc.

Presently, routine clinical implementation of the above-described techniques suffers from drawbacks in that they: (a) are labor intensive; (b) require human judgment; and (c) require delivery of radiation before patient/field position can be determined. In addition, most analysis is done off-line after patient treatment has been completed.

At present, no commercial system exists which can rapidly, reliably, remotely and accurately measure the orientation/position of a patient in Cartesian space by performing the following tasks: (a) resolve target position on a patient to better than 1 mm absolute in Cartesian space and determine patient rotation about any of the three principal axes; (b) provide sufficient reproducibility so that an operator/technologist can reposition targets on the patient with a reproducibility of better than 2 mm, from day to day; (c) warn the operator/technologist if the patient, i.e., the targets, are not in the correct position before treatment; (d) report patient position with respect to an initial, i.e., reference, patient setup or with respect to a setup for a particular treatment; and (e) provide a method for quality assurance of a linac ODI, laser, light field position and digital couch. Thus, there is a need in the art for a system for accurate patient setup and day-to-day patient position verification which provides these capabilities.

SUMMARY OF THE INVENTION

Advantageously, embodiments of the present invention solve the above-identified problems by providing a remote sensing system capable of real time monitoring of patient position which can report variations in patient setup from day to day as well as motion during individual treatments. In particular, an embodiment of the present invention is a system which can rapidly, reliably, remotely and accurately measure the orientation/position of a patient in Cartesian space by performing the following tasks: (a) accurately resolve target position on a patient, e.g., to better than 1 mm absolute, in Cartesian space and determine patient rotation about any of the three principal axes; (b) provide sufficient reproducibility so that an operator/technologist can reposition targets on the patient with high reproducibility, e.g., of better than 2 mm, from day to day; (c) warn the operator/technologist if the patient, i.e., the targets, are not in the correct position before treatment; (d) report patient position with respect to an initial, i.e., reference, patient setup or with respect to a setup for a particular treatment; and (e) provide a method for quality assurance of a linac ODI, laser, light field position and digital couch. Specifically, an embodiment of the present invention comprises: (a) a source of radiation for applying radiation to a patient; (b) target means affixed to the patient for reflecting radiation impinging thereon; (c) camera and computer means for detecting the reflected radiation and for determining the position of the targets in three-dimensional space; (d) data storage means for storing the position of the targets; (e) computer means for comparing the position of the targets with positions stored in the data storage means; and (f) display means for displaying indicators whenever differences between the position and the stored position exceed tolerances stored in the data storage means.

In accordance with further embodiments of the present invention, an inventive user interface enables a user to define tolerance tables for position differences based on clinical application where, for example, a stereotactic motion tolerance table may be assigned a tighter tolerance than that required for breast setup. Further in accordance with the present invention, displays are made of position differences which exceed predefined tolerance values wherein a displays of predetermined colors, such as a red bar, indicate the severity of position mismatches. Still further in accordance with the present invention, displays of patient motion are made, which displays can be stored and/or printed.

In particular, embodiments of the present invention comprise a computerized video based system capable of measuring Cartesian coordinates of small optical targets placed on a surface of a patient and a user interface and analysis software package. A preferred embodiment of the inventive system comprises two CCD cameras mounted in a treatment roomed and focused on a treatment unit isocenter. The cameras are interfaced to a 486 33 MHz PC via a two channel video board. Inventive passive targets (retroreflective in the preferred embodiment) are attached to a surface of the patient. The targets are automatically recognized and extracted by a three-dimensional (3-D) vision system and the three-dimensional position of each target is determined using a triangulation algorithm. When the patient moves, the system senses motion of the targets and reports a change in patient position. When the targets are placed in the same position on the patient, from day to day, in accordance with a preferred embodiment of the present invention, patient setup is reproducibly determined.

As those in the art can readily appreciate, embodiments of the present invention advantageously enable the positions of the targets, and by inference the patient, to be determined accurately before radiation is delivered. In addition, in accordance with such embodiments, relative motion, i.e., setup position, of the patient from day to day is determined.

For a fuller understanding of the present invention, reference should now be made to the following detailed description of the preferred embodiments of the invention and the accompanying drawings.

BRIEF DESCRIPTION OF THE FIGURE

FIG. 1a shows, in pictorial form, a target for use in an embodiment of the present invention;

FIG. 4 shows base line length B between cameras 150 and 160 and standoff distance S.

DETAILED DESCRIPTION

Figure 1:
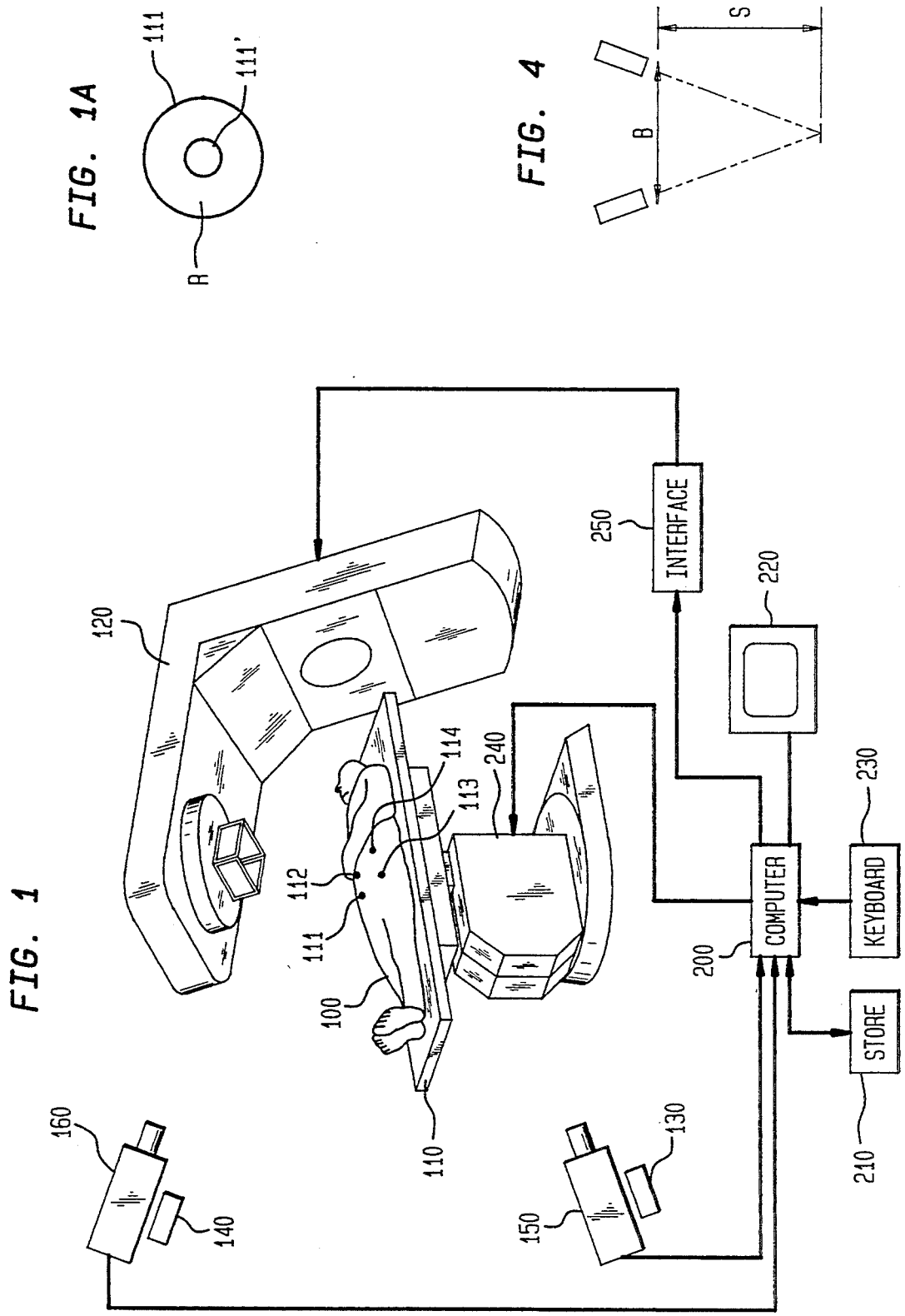
FIG. 1 shows, in pictorial form, an embodiment of the present invention.

FIG. 1 shows, in pictorial form, an embodiment of the present invention. As shown in FIG. 1, a patient 100 lies on table 110 under gantry 120 of a radiation therapy machine. Targets 111–114 have been affixed to the chest of patient 100. As will be described in detail below, in a preferred embodiment of the present invention, targets 111–114, formed of retroreflective material which is disposed on one side of a substantially flat tape and a pressure sensitive adhesive tape disposed on the other side, are affixed to the patient.

Light sources 130 and 140 provide radiation which impinges upon targets 111–114. In the preferred embodiment of the present invention, light sources 130 and 140 produce infrared radiation. Infrared radiation is advantageous in that it enables the system to more readily distinguish light reflected from the targets, as opposed to background radiation (interference) that might be available in a therapy room under ambient lighting conditions. In the preferred embodiment, light sources 130 and 140 are infrared lasers which are commercially available and whose radiation is spread by lenses so as to illuminate targets 111–114. The use of laser light sources is advantageous in that the spectral bandwidth of the radiation is narrow and provides, thereby, a further reduction in background interference.

Cameras 150 and 160 are focused substantially on table 110 and are standard 512×480 pixel CCD cameras which are commercially available. (Alternatively, higher resolution cameras, such as 1320×1035 pixels available from Videk Megaplus may be used.) In the preferred embodiment, the cameras are equipped with infrared filters to further reduce detection of background radiation. Further, the cameras are fixed in position so that they do not have to be recalibrated often in accordance with the method described in detail below. The outputs from cameras 150 and 160 are applied to image acquisition and processing boards (not shown) which are disposed within a PC-type computer 200. In the preferred embodiment, the image acquisition boards were purchased from Matrox Corporation as IM-1280 with ASD digitizer and RTP board. Computer 200 is associated with store 210 which is used to store software used in operating computer 200 and is used to store data received from cameras 150 and 160, from users inputting data from a keyboard 230, and data produced, in a manner which will be described in detail below in accordance with the present invention, by computer 200. A display 220 is utilized to provide the results of analyses, in a manner which will described in detail below in accordance with the present invention, by computer 200.

Interface 250 provides communication between the therapy machine, of which gantry 120 forms a part, and computer 200, which communication will be described in detail below. Further, positioning apparatus 240 is configured to receive positioning signals from computer 200 in order to adjust the position of table 110 and, thereby, patient 100 in a manner which will be described in detail below.

Embodiments of the present invention include a Vision-based Coordinate Measurement (VCM) system which is used to measure the positions of the targets. The VCM software is comprised of a set of library routines which are utilized to design application programs and to combine the application programs with application-specific user interface software. In accordance with a preferred embodiment of the present invention, the library routines are dynamic link libraries (DLLs) written in C for Microsoft Windows. The VCM system has been under development at the National Research Council of Canada for several years and has been described in an article entitled "A Hierarchical Approach to Stereo Vision" by El-Hakim, S. F., *Photogrammetric Engineering and Remote Sensing*, 55(4), 443–448 (1989), an article entitled "The VCM Automated 3-D Measurement System—Theory, Application, and Performance Evaluation" by El-Hakim, S. F., *Applications of Artificial Intelligence X: Machine Vision and Robotics, Proc. SPIE* 1708, 460–482 (1992), and an article entitled "Multicamera Vision Based Approach to Flexible Feature Measurement For Inspection and Reverse Engineering" by El-Hakim, S. F. and Pizzi, N.J., *Optical Engineering*, 32(9), 1993, all three articles being incorporated herein by reference. As shown in the above-described articles, the VCM system is a software package which can be integrated with commercially available solid-state cameras, image grab and processing boards, and computer hardware. As is described in these references, the VCM system combines principals of stereo vision, photogrammetry and knowledge-based techniques to provide precise coordinate and dimension measurements of objects. As will be described in further detail below, the VCM system is used to measure the positions of targets 111–114 placed on a surface of patient 100. Note that the VCM system has been used for other medical applications, including measurement of orthopedic seats and anatomical stumps as described in an article entitled "Implementation of a 3-D Stereovision System for the Production of Customized Orthotic Accessories" by Daher, R., McAdam, W., and Pizey, G., *Industrial Vision Metrology, Proc. SPIE* 1526, 90–95 (1991).

The target extraction and measurement method used by the VCM system has been described in detail in the above-described El-Hakim references. The method is comprised of several hierarchical steps. In accordance with the method, camera images are received and a step of segmentation processing reduces an image into a binary image using an automatic thresholding routine. Then, in the next step, target candidates are isolated by performing connectivity analysis to separate images into blobs. Blob parameters such as area, perimeter, and radius are used to identify targets whose positions are to be determined. Next, subpixel target positions are determined using centroids or by using edge fitting techniques; in accordance with the VCM system, this step uses the original gray-scale image rather than the binary image and a correction, due to circle projections into the image, is applied to the centroid. In the next step, targets from different camera images are matched using constraints to aid in the matching process. Finally, after targets from different camera images have been matched, their 3-D positions are determined using camera calibration parameters and triangulation methods.

In accordance with the present invention, the iterative, hierarchical matching process described above is controlled by sets of constraints determined by scene and sight intensity, geometric relationships, and a prior knowledge. A first constraint is referred to as an epipolar line constraint: In accordance with this epipolar line constraint, to match a point in a first image with its corresponding point in a second image, the image coordinates of the point in the first image and calibration parameters of the two images are used to determine the relationship between x and y coordinates of the corresponding point in the second image. This is a straight-line equation, and the image coordinates of all recognized points in the second image are tested to determine which one falls on this line. A second constraint is referred to as a disparity constraint. In accordance with this disparity constraint, the expected range of disparity, i.e., the difference between x-coordinates from the two images, is computed from two sources. A third constraint is a depth constraint which uses a known a priori expected range of depth as determined from the setup procedure and the already successfully matched points in earlier iterations. A final constraint or ordering constraint is applied if more than one point satisfies the above constraints.

In accordance with the present invention, reasonably rigorous camera calibration is essential where accurate measurement is required and to ensure successful stereo matching. As is well known, calibration is required to determine: (a) the position and orientation of a camera with respect to a selected coordinate system, (b) focal length and coordinates of a principal point on an image, and (c) parameters to compensate for distortions produced by lenses, pixel size, alignment, and so forth. In accordance with a preferred embodiment of the present invention, the calibration approach used implements no or minimum approximations to provide an accurate solution, with no restrictions on the distortion model. Advantageously, in the patient position monitoring system fabricated in accordance with the present invention, the camera setup does not change and the environment is largely structured. Thus, a calibration should be valid for long periods of time. As a result, a recalibration need only be performed if the system has failed a quality assurance check or after a camera position has been altered. In the preferred embodiment of the present invention, position calculation is performed in accordance with methods which are well known in the art and which will only be summarized here. One example of such method is described in Chapter 5 of "The Handbook of Non-Topographic Photogrammetry, 2nd ed.," Karara, H. M, ( ed. ), *American Society of Photogrammetry and Remote Sensing*, (1989), which book is incorporated by reference herein. Position calibration is performed in accordance with equations (1)–(4).

$$x - x_0 + dx = \quad (1)$$

$$-f \frac{(X - X_0)m_{11} + (Y - Y_0)m_{12} + (Z - Z_0)m_{13}}{(X - X_0)m_{31} + (Y - Y_0)m_{32} + (Z - Z_0)m_{33}}$$

$$y - y_0 + dy = \quad (2)$$

$$-f \frac{(X - X_0)m_{21} + (Y - Y_0)m_{22} + (Z - Z_0)m_{23}}{(X - X_0)m_{31} + (Y - Y_0)m_{32} + (Z - Z_0)m_{33}}$$

where:

$m_{ij}$ (i,j=1, 2, 3) are elements of a camera rotation matrix and are functions of three spatial rotation angles; X, Y, and Z are object coordinates of a point; x and y are corresponding image coordinates; $X_0$, $Y_0$, and $Z_0$ are the camera projection center coordinates; $x_0$ and $y_0$ are the principal point coordinates; and f is the focal length.

Finally, dx and dy are functions of distortion parameters and are given by:

$$dx = a_1 y' + x'(a_3 r^2 + a_4 r^4) + a_5(r^2 + 2x'^2) + 2a_6 x' y' \quad (3)$$

$$dy = a_2 y' + y'(a_3 r^2 + a_4 r^4) + a_6(r^2 + 2y'^2) + 2a_5 x' y' \quad (4)$$

where:

r is the radial distance from an image point to the principal point; x' and y' are components of this distance; $a_1$ and $a_2$ are distortion parameters which correct for affine scale and non-perpendicularity of image axes; $a_3$ and $a_4$ are distortion parameters which correct for radically symmetric lens distortion; and $a_5$ and $a_6$ are distortion parameters which correct for decentering lens distortion which results from misalignment of the centers of the lens components or from non-perpendicularity of an optical axis to the image plane.

Figure 2:
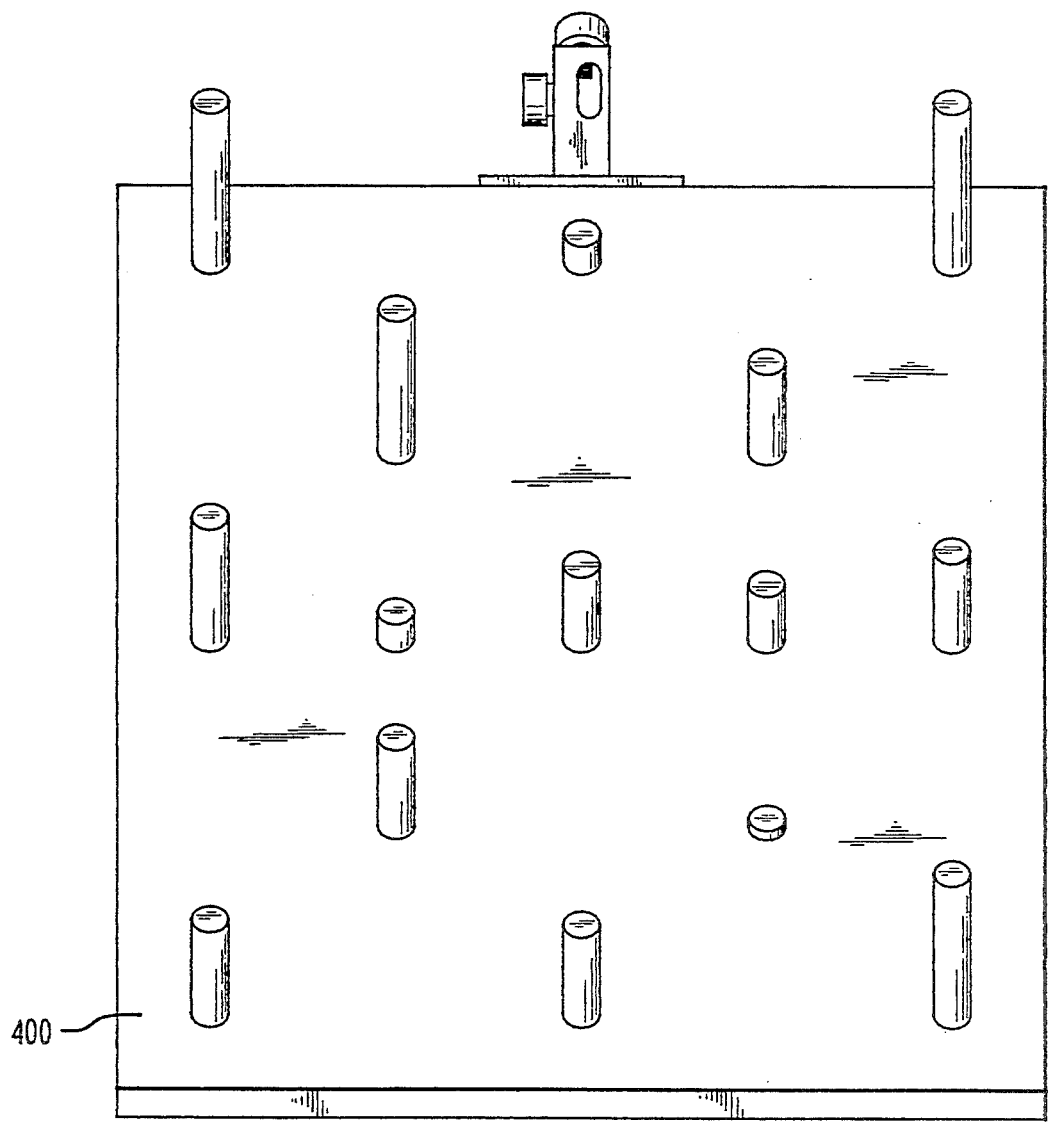
FIG. 2 shows a device comprised of a set of well-defined targets mounted at various heights disposed on one side of a thermally stable plate which is used for calibration in an embodiment of the present invention.

The above described calibration requires control points of precisely known positions in the object space coordinate system. FIG. 2 shows a device comprised of a set of well-defined targets mounted at various heights disposed on one side of a thermally stable plate which is used in a preferred embodiment of the present invention. As shown in FIG. 2, thermally stable plate 400 comprises a thick slab of aluminum.

As is well known, for the calibration process: X, Y and Z of the control points are known and image coordinates x and y are measured, while all other parameters (in the preferred embodiment of the present invention 15 parameters per camera are used) are unknowns and solved for. Since each control point contributes two observation equations, a minimum of eight points are required and an iterative least-squares adjustment solution is carried out to solve for the unknowns parameters.

In accordance with a preferred embodiment, the two cameras and 3-D vision software are calibrated such that their frame of reference is coincident with that of the therapy unit, with an isocenter defined as 0,0,0. The coordinate system is defined such that: (a) the X axis lies in a horizontal plane perpendicular to the gantry axis of rotation and passes through the isocenter; (b) the Y axis is parallel to the gantry axis of rotation and passes through the isocenter; and (c) the Z axis is mutually perpendicular to the other two axes and defines patient height.

A user interface for the preferred embodiment of the present invention was developed in visual basic to run under Microsoft Windows 3.1. It is a menu driven system which provides drop down windows which are well known in the art. As will be described below, the system comprises a data base for storing patient demographics and patient position data.

In routine use, the operator/technologist affixes from three to five targets on a patient's surface. In the preferred embodiment of the present invention, the targets are substantially circular paper targets, such as shown by target 111 in FIG. 1a, and have an approximately 12.5 mm diameter. The targets 111 have a pressure sensitive adhesive back to ensure that they do not move during each portion of the treatment plan. Typically, the targets are removed after each treatment and replaced the following day. As also shown in FIG. 1a, the center of the targets have an approximately 2.0 mm diameter, substantially circular hole 111; which hole provides a means which is used by the operator/technologist to relocate the targets at the same place on the patient's surface from day to day. This is done by visually locating a mark placed on the patient during a therapy simulation process, which procedure is well known to those of ordinary skill in the art. During the simulation process, a mark is, for example, tattooed on the patient. Then, during the therapy session, the tattoo marks are visually aligned with the above-described hole in the target. It should be appreciated that the hole in the target need not be circular and may assume a number of other shapes that could be used to perform a similar purpose and, instead of being a hole, an area of the target may be made so thin as to permit visual sighting of a marker therethrough by, for example, inspection with a handheld light. Advantageously, in accordance with the preferred embodiment of the present invention, placing the targets requires approximately 15 seconds per patient measuring and reporting patient position (displacement and rotation) takes place in less than about 5 seconds.

In the preferred embodiment of the present invention, the targets shown in FIG. 1a are comprised of a retroreflective material R, as shown in FIG. 1a, deposited on one side of a paper base, with an adhesive, not specifically shown, deposited on the side of the paper base which is opposite the illustrated side having the retroreflective material R. The retroreflective material R is useful to reduce the background. Retroreflective materials are well known in the art and are commercially available (for example, an appropriate retroreflective tape is available from the 3M company of Minnesota). When utilizing a retroreflective material, light source 130 and 140 are positioned close to cameras 150 and 160, respectively so that radiation reflected from the target is detected by the camera.

Note that it is within the spirit of the present invention that the targets be comprised of phosphorescent material which emit radiation, in place of the retroreflecting material R shown in FIG. 1a. In such embodiments, the phosphorescent material can be stimulated in accordance with methods which are well known to those in the art by, for example, illumination by radiation prior to or after being affixed to the patient. Such targets would be advantageous in reducing background in that filters can be utilized to provide camera sensitivity to radiation in the band of radiation produced by the phosphorescent material. Further, in such an embodiment, one may eliminate light sources 130 and 140 or one may utilize a single light source which need not be placed near the camera. In a similar vein, one can utilize targets comprised of a fluorescent material which are then irradiated with a source which causes the generation of fluorescent radiation. Again, the cameras could be equipped with filters to enhance selectivity of reception. In such an embodiment one could utilize a single source for irradiation.

In accordance with the present invention, the targets utilized for calibration shown in FIG. 2 need not be fabricated as described above and may be, for example, fabricated from plain white paper since the calibration is typically performed under controlled conditions and reflections from a patient which might simulate a target is substantially less likely. Further, such targets may even be used for the patient as long as reflections from other objects is carefully monitored. Still further, sources 130 and 140 may even be sources of white light as long as ambient conditions are carefully controlled. However, the preferred embodiment is expected to be used in most applications where it is advantageous that ambient conditions of lighting and so forth not have to be extremely strict.

In accordance with the present invention, three types of patient position data are measured and recorded: (a) reference data; (b) setup data; and (c) treatment data. The reference data are coordinates of each target on the patient, in 3-D space, which are measured, for example, at the time of the patient's initial treatment setup or simulation. There is one set of reference data for each isocenter. Setup data are coordinates of each target on the patient, in 3-D space, which are measured prior to therapy to provide an opportunity to determine and adjust the patient's position before radiation is delivered. Lastly, treatment data are the coordinates of each target on the patient's surface, in 3-D space, which are measured every five seconds while the therapy beam is on. The treatment data provides a real time report of deviations between the reference position and the placement of the patient during each treatment. Advantageously, use of embodiments of the present invention in connection with simulator and treatment units assures substantially identical coordinate systems in each so that patients can be transferred between units while still using the same target position information.

In accordance with the present invention, an error in patient position, as determined from the treatment data with respect to the reference data ,is calculated such that the deviation in the x direction, $\underline{X}_{dev}$, is given as:

$$X_{dev} = \frac{\sum\limits_{i=1}^{N} X_{io} - X_i}{N} \tag{5}$$

where:

$X_{i0}$ is the absolute reference position of the ith target and $X_i$ is the absolute position of the ith target at setup.

Deviations in the Y direction and the Z direction are calculated in a similar manner. Then, the total deviation $R_{dev}$ is calculated as follows:

$$R_{dev} = \sqrt{X_{dev}^2 + Y_{dev}^2 + Z_{dev}^2} \tag{6}$$

In order to implement eqn (5), it is necessary to be able to uniquely identify each target. As one can appreciate, target identification ensures that the relative positions of the targets placed on the surface of the patient for a specific treatment coincide with the targets measured at the time the reference data were determined. In accordance with the present invention, target identification is performed by an algorithm which performs two functions: (a) discarding extraneous targets reported by the VCM output and (b) matching targets measured at treatment time to those measured at the time the reference setup was established. In accordance with the present invention, the method of identifying targets proceeds as follows. Let $r_{i,j}$ denote a vector joining the ith and jth target identified when the reference position was measured. Similarly, let $v_{k,l}$ denote a vector joining the kth and lth targets measured at treatment time. Then, target identification depends on a correspondence of those relative vectors with each other. That means, if $r_{i,j}$ and $v_{k,l}$ are equal then target k is taken to correspond to target i and similarly for 1 to j. The equivalence of the relative vectors are assumed if:

$$||r_{i,j} - v_{k,l}|| < e_1 \text{ and } ||\psi|| < e_2 \qquad (7)$$

where:

$e_1$ and $e_2$ are target placement tolerances and $\psi$ is the angle between vectors $r_{i,j}$ and $v_{k,l}$.

Angle $\psi$ is determined in accordance with the following equations:

$$\psi = \pi - \cos^{-1}\left(\frac{r_{i,j} \cdot v_{k,l}}{||r_{i,j}||\ ||v_{k,l}||}\right) r_{i,j} \cdot v_{k,l} < 0 \qquad (8)$$

$$\psi = \cos^{-1}\left(\frac{r_{i,j} \cdot v_{k,l}}{||r_{i,j}||\ ||v_{k,l}||}\right) r_{i,j} \cdot v_{k,l} > 0 \qquad (9)$$

Note that the sense of the relative vectors is important in determining target coincidence. Although the target identification algorithm is fairly robust, it will fail under certain circumstances. For example, the algorithm could report ambiguous results where the targets have been placed in an axially symmetric pattern. Thus, in utilizing the present invention, placement of targets in an asymmetric pattern will preclude this problem.

Patient rotation is specified using the terminology tilt, roll and yaw which are defined as rotations about axes parallel to the principal X, Y, and Z axes, respectively. In accordance with the present invention, patient tilt and roll are calculated from differences in normals to the best fit planes (by least squares fit) through all of the targets at reference and treatment (setup), respectively. The differences between the reference angles and the angles at the time of treatment or setup provide the patient rotation information. Patient Yaw is defined as:

$$Yaw = \frac{\sum_{i=1}^{n} \theta_{oi} - \theta_i}{N} \qquad (10)$$

where $\theta_{oi}$ is given as:

$$\tan^{-1}\frac{(Y_{oi} - Y_{0cm})}{(X_{0i} - X_{0cm})} \qquad (11)$$

and $Y_{0cm}$ and $X_{0cm}$ are the x,y co-ordinates of the center of mass of the reference targets. $\theta_i$ is given similarly using its own center of mass as a reference.

Note that, in general, the center of mass of the targets does not lie on the room Z axis. Thus, a transform matrix is calculated from Yaw, $X_{dev}$, and $Y_{dev}$, to move the patient back to the reference position using only table motions. Such table motions are relayed to apparatus 240 on table 110 from computer 200. Apparatus 240 is apparatus which is well known to those of ordinary skill in the art for moving table 110 in cartesian space. In the absence of apparatus 240 to perform table motions in response to signals transmitted thereto from computer 200, the appropriate table motions may be performed by the operator/technologist using output provided on display 220 (of course display 220 may comprise a standard CRT display and, optionally, a printer). Table motions to correct for tilt and roll are relayed to apparatus 240 on table 110 from computer 200. In the absence of apparatus 240 to perform table motions to correct for tilt and roll, the appropriate table motions may be performed by the operator/technologist using output provided on display 220 by rotation of the patient about axes passing through the center of mass of the targets.

Figure 3:
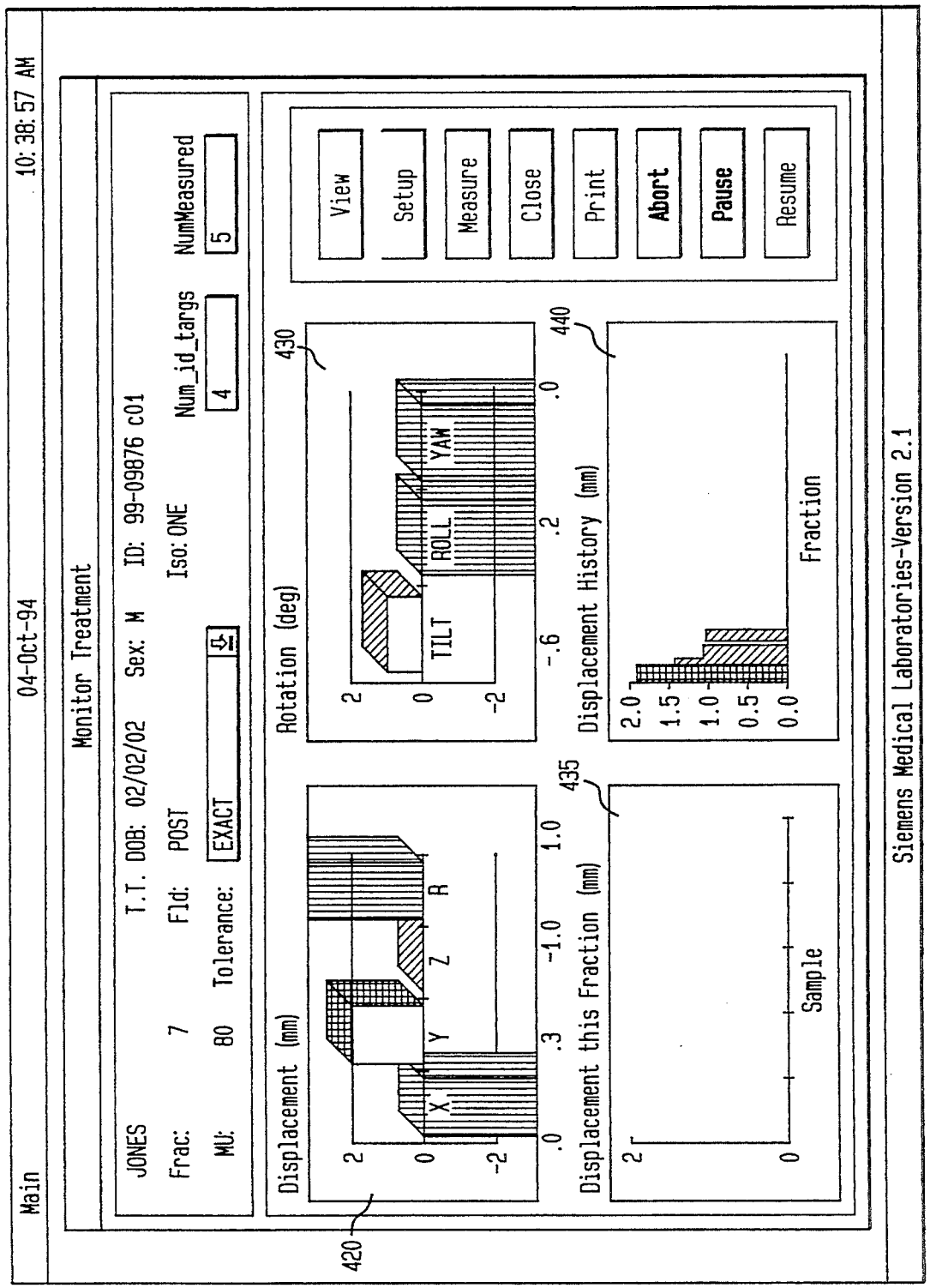
FIG. 3 shows an example of the display of patient treatment and position in accordance with the present invention.

Patient treatment and position are displayed to the operator/technologist on display 220 in a format such as that shown in FIG. 3. In accordance with the present invention, real time deviations in displacements (X,Y,Z, and R) and rotations about the three principal angles are displayed as colored bars whose lengths are proportional to the magnitude of the deviation. In accordance with a preferred embodiment of the present invention, the bars are color coded such that displacements which exceed tolerances requested by a radiation oncologist are displayed in red, deviations which are greater than some operator selected percentage (for example, 80%) of the allowed tolerance are displayed in yellow as a warning, and deviations less than that are displayed as green. Both the tolerances (red) and warning level (yellow), as a percentage, are user definable and selectable at run time from a list. The user interaction for selecting such information is provided in a combination of a Window-type format pull-down list and operator fill in mode utilizing keyboard 230. In addition to instantaneous treatment data shown in upper left block 420 and upper right block 430 of FIG. 3, a time history of displacement vector R for this fraction is shown in lower left block 435. Lastly, a history of the magnitude of vector $R_{av}$ (the average error for each previous fraction already delivered) is shown in lower right block 440. The historical data, setup data and reference data for a patient are stored in data store 210 which, in the preferred embodiment is a hard disk. In further embodiments of the present invention, data relating to patients may be transmitted by means of communications links to data bases for analysis by other people, for maintaining records of treatment verification, and so forth. Communications links for performing such data transfers are well known to those in the art.

In addition to the above, in accordance with the present invention, in connection with the user interface, the operator/technologist can specify treatment fractions for various radiation beam treatments. In such a mode, computer 200 keeps track of the fraction and, for example, the time required by the radiation machine to deliver the predetermined treatment fraction. In response to a signal, for example, from the operator/technologist that treat ought to begin, computer 200 sends a signal to apparatus 250 in the radiation machine to, for example, close a switch to enable treatment to commence. When computer 200 determines that the treatment time has elapsed for the selected fraction, a further signal is sent to apparatus 250 to, for example, open a switch to cease treatment. If radiation machine is not equipped with an apparatus 250 for activating/deactiating in response to signals from computer 200, then computer 200 may display a signal which indicates that a sufficient time for the selected treatment fraction to have occurred has elapsed. Such a display could also be utilized when apparatus 250 were available. In accordance with the present invention, the display signals includes a visual display on a CRT or a printer as well as an audible signal which is generated in accordance with methods which are well known in the art. For example, most PC computers are equipped with the ability of generating an audible signal.

We have built an embodiment of the present invention and tested the target position measurement portion in a laboratory. The laboratory tests had the following objectives: (a) to establish the best geometrical configuration for camera setup; (b) to determine the statistical stability (precision) of measurements under a variety of conditions; and (c) to determine measurement bias relative to an independent measurement system. For the laboratory measurements, we used a co-ordinate system such that X was defined by a vector between cameras 150 and 160, Y was defined as being mutually perpendicular to X and a plane containing the central axis of vision of cameras 150 and 160. Z lies in the plane and is mutually perpendicular to X and Y. A three-axes (XYZ) positioning stage was used as an independent measurement system for comparison with the VCM system measurements. A complete description of test results are found in an article entitled "Performance Evaluation of a Vision Dimension Metrology System" by El-Hakim, S. F. and Westmore, D. B., *Industrial Vision Metrology, Proc. SPIE* 1526, 56–67, (1991).

In order to ensure random sampling while repeating the measurements to compute the mean and standard deviation, realistic variations in conditions must by used. Four or more independent measurements must be made in order to have a representative sample (see an article entitled "Realistic Evaluation of the Precision and Accuracy of Instrument Calibration Systems" by Eisenhart, C., *J. of Research of the National Bureau of Standards-C. Engineering and Instrumentation,* 67C(2), 161–187 (1963)). It is also important to compute the vision system bias as the difference between the mean of the measured value and the value obtained by the independent system.

Before evaluating the accuracy, i.e., precision and bias of measurements, of the measuring system, a set of 15 targets, substantially 1 cm in diameter, covering a volume of 30 cm $\times$ 30 cm $\times$ 20 cm with accurately know 3-D coordinates shown in FIG. 2 was used for a preliminary test. In this preliminary test, the positions of the 15 targets were measured with a coordinate measuring machine (CMM) which had an accuracy of 5 microns. A standoff distance, defined as the difference between the Z coordinate of a camera and the average z value of the targets, was calculated from system measurement data to determine the effect of a ratio between the length of the base-line of the two cameras and object standoff distance. This effect was studied by varying the length of the baseline, re-calibrating the system, and then measuring the same 15 points using the re-calibrated parameters. The root mean square value (RMS) of differences between the given values and those measured by the system was then computed. We determined that the Z-coordinate was systematically affected by the ratio of base-line length to object standoff, while X and Y-coordinates remained virtually constant. The best results were obtained for a ratio of approximately 0.7 or larger, or at a convergence angle between the two cameras of at least 38.6 degrees. This configuration was then used for all subsequent tests. FIG. 4 shows base line length B between cameras 150 and 160 and standoff distance S.

In performing tests to examine repeatability, i.e., precision, the coordinates of a single target, measuring 1 cm in diameter, was measured 10 times and the standard deviation was computed. The test was repeated on each target in the set of 15 targets which were distributed over the entire common viewing field of the cameras. The results of these measurements are that measurements of the 15 targets showed little variation. This level of reproducibility is not always guaranteed, as demonstrated by the higher standard deviation obtained on a single target. In light of this, it is important to examine deviations in local regions of view separately instead of examining global measures over the entire image area. In performing tests to examine bias, the XYZ stage of a therapy system was mounted with the set of 15 targets and tests were performed. The RMS values of the differences between known target positions and measured values were 0.015 mm, 0.014 mm and 0.032 mm for X, Y, and Z respectively. Smaller deviation could be achieved by tightening the range of allowable variation in the fitting and target parameters. In addition, we have determined that measurement bias was significantly larger for targets lying near the image periphery. This result is probably due to uncorrected systematic errors that increase as a function of the distance from the image center, error in the reference XYZ-stage itself near its maximum traveling distance, or variations in light intensity near the image periphery.

We have performed clinical trials which show repositioning accuracy of the patient with respect to treatment beams to be better than 2.1 mm.

We have determined that lighting conditions strongly effect the ability of the VCM to recognize and extract targets placed on the patient surface. As such, it was not possible to use the inventive system to measure the patient position during the setup while room lights were off and only the linac field light visible. In addition, we have discovered that problems exist whenever objects are present which provide high reflection. Further, geometric restrictions of a radiation therapy room impose significant constraints on camera placement. In an ideal environment, the camera would be placed above the patient on either side of the isocenter in the plane $Y=0$, such that the angle subtended at the patient by the cameras would be greater than 38.6 degrees. However, several clinical and environmental constraints exist which make this impossible. First, the cameras must have a view of the patient in the vicinity of the isocenter, independent of gantry angle. This requires that the camera be moved forward away from the gantry. The second problem arises from the fact that the patient surface is curved and the cameras have an oblique view of the patient. This restricts the area on the patient's surface which is suitable for target placement, since each target must be visible to both cameras. We have found that optimal camera placement is a trade off between optimizing the metric performance of the VCM system and providing an optimal view of the patient's surface. For the clinical environment tested, i.e., a Siemens KD2 in a therapy room with a ceiling height of 3.4 m, we have found that the optimal camera placement is at a height of 1.6 m above isocenter, 1.02 m laterally (X) on either side of isocenter, and 1.6 m forward of isocenter.

The optimal metric performance of the VCM algorithms and the specific hardware used for this application can be summarized as follows: (a) the precision or repeatability has a standard deviation of 0.008 mm (1:31000) in x, y and 0.014 mm in z (1:18000) and (b) in terms of system bias, the RMS of comparative measurements differences were 0.014 mm (1:18000) in x, y and 0.032 mm in z (1:8000). This optimal performance occurred for conditions where the field of view was 30 cm×30 cm×20 cm, a base-to-standoff ratio of at least 0.7, and the target was at least 25 mm inside the field of view. In addition, we have found that for optimal performance, each measurement should be repeated at least four times and averaged. A single measurement results in a maximum error of 0.03 mm under ideal conditions.

Those skilled in the art will recognize that the foregoing description has been presented for the sake of illustration and description only. As such, it is not intended to be exhaustive or to limit the invention to the precise form disclosed. For example, modifications and variations are possible in light of the above teaching which are considered to be within the spirit of the present invention. Thus, it is to be understood that the claims appended hereto are intended to cover all such modification and variations which fall within the true scope and spirit of the invention.

What is claimed is:

1. Apparatus for monitoring and sensing changes in position of a patient from a prior position at a prior time to a current position at a current time, which apparatus comprises:
    a source of radiation for applying radiation to a patient;
    a plurality of individual targets adapted to be releasably affixed at both a current time and a prior time to the patient, for reflecting radiation impinging thereon;
    camera and computer means for detecting the reflected radiation from individual ones of the targets, uniquely identifying individual ones of said targets from which radiation was detected, and for individually determining current and prior positions of the uniquely identified targets in three-dimensional space, based on the target fixation to the patient at the current and prior times, respectively;
    data storage means for storing data representative of at least the prior position of the uniquely identified targets;
    computer means for comparing the current position of the uniquely identified targets with the prior position data stored in the data storage means for those identified targets, and developing from said comparing position signals representative of a difference in position of said identified targets, and therefore said patient from said prior time to said current time; and
    display means responsive to said position signals for displaying indicators representative of said difference in position of said patient.

2. The apparatus of claim 1 which further comprises means for user interaction for receiving and storing data from the user, the data comprising user-set tolerances; and wherein the display means displays the indicators so that they have a size which is proportional to the magnitude of the difference, and a color which is dependent upon the magnitude that the difference exceeds a percentage of the tolerance stored in the data storage means.

3. The apparatus of claim 2 which further comprises means for sending a position signal to a table means which supports the patient, wherein
    the table means, in response to the position signal, comprises means for moving the patient so that the differences do not exceed the tolerances.

4. The apparatus of claim 2 wherein the display means comprises means for displaying an indicator in a first color if the difference exceeds a first limit and in a second color if the difference exceeds a second limit.

5. The apparatus of claim 2 wherein the display means further comprises means for displaying the differences in a predetermined color if the differences do not exceed the tolerance.

6. The apparatus of claim 1 wherein the data further comprises a treatment fraction requirement for a user defined modality of treatment and wherein the computer means further comprises means for comparing the treatment fraction with a time of application of radiation and means for signaling the operator that the time of treatment for the fraction has expired.

7. The apparatus of claim 1 wherein the data further comprises a treatment fraction requirement for a user defined modality of treatment and wherein the apparatus further comprises means for signaling that a radiation therapy machine is active and the computer means further comprises:
    means for receiving the signal and determining a time of radiation;
    means for comparing the treatment fraction with the time of radiation and means for signaling the operator that the time of treatment for the fraction has expired.

8. The apparatus of claim 7 which further comprises means for sending a turnoff signal to the radiation therapy machine for causing the radiation therapy machine to cease being active.

9. The apparatus of 6 wherein the computer means for comparing further comprises:
    means for storing the fraction of treatments provided for a patient in the storage means for each treatment along with an indicator of the data of the treatment;
    means for displaying the stored treatment fractions and sums of the treatment fractions.

10. The apparatus of claim 5 wherein the predetermined color is green.

11. The apparatus of claim 4 wherein the first color is orange and the second color is red.

12. The apparatus of claim 4 wherein the first limit comprises a first percentage of the tolerance and the second limit comprises a second percentage of the tolerance.

13. The apparatus of claim 1 wherein the source of radiation comprises a source of infrared radiation.

14. The apparatus of claim 1 wherein the camera means comprises CCD camera means.

15. The apparatus of claim 14 wherein the camera means further comprises infrared filter means.

16. The apparatus of claim 1 wherein the target means comprises retroreflective reflector means.

17. The apparatus of claim 16 wherein the retroreflector means comprises at least one reflector, the reflector being comprised of a first portion which is retroreflective and a second portion which is not retroreflective.

18. The apparatus of claim 17 wherein the first portion has a first predetermined shape and the second portion has an aperture, wherein the aperture is large enough so that a mark placed the surface of the patient may be seen when the target is affixed to the patient.

19. The apparatus of claim 1, wherein a target comprises:
- a body of substantially flat material;
- means disposed on one side of the body for releasably affixing the body to a patient; and
- means disposed on the other side of the body for retroreflecting radiation; wherein:
- the retroreflecting means comprises a first portion which is retroreflective and a second portion which is not retroreflective.

20. The target of claim 19 wherein the first portion has a first predetermined shape and the second portion has an aperture, wherein the aperture is large enough so that a mark placed on the surface of the patient may be seen when the target is affixed to the patient.

21. The apparatus of claim 2 wherein the targets comprises at least three reflectors and wherein the computer means further comprises means for determining a position of a plane of at least three of the at least three reflectors.

22. The apparatus of claim 21 wherein the targets comprises more than three reflectors and the computer means further comprises means for determining a plane by a least squares fit between planes determined by groups of three reflectors.

23. The apparatus of claim 2 wherein the computer means further comprises means for determining a position of the patient as a center of mass of the Positions of the targets.

24. Apparatus for monitoring and sensing changes in position of a patient from a prior position at a prior time to current position at a current time, which apparatus comprises:
- a plurality of individual phosphorescent targets adapted to be releasably affixed to the patient at both the current time and the prior time, for generating radiation;
- camera and computer means for detecting the radiation from individual ones of the targets, uniquely identifying individual ones of said targets from which radiation was detected, and for individually determining current and prior positions of the uniquely identified targets in three-dimensional space, based on the target fixation at the current and prior times;
- data storage means for storing data representative of at least the prior position of the uniquely identified targets;
- computer means for comparing the current position of the uniquely identified targets with the prior position stored in the data storage means for those identified targets, and developing from said comparing position signals representative of a difference in position of said identified targets, and therefore said patient, from said prior time to said current time; and
- display means responsive to said position signals for displaying indicators representative of said difference in the position of said patient.

25. The apparatus of 24 wherein the camera means further comprises filter means for passing radiation substantially in the range of wavelengths emitted by the targets.

26. The apparatus of claim 24 wherein the phosphorescent means comprises at least one generator, the generator being comprised of a first portion which is phosphorescent and a second portion which is not phosphorescent.

27. The apparatus of claim 24, further comprising:
- means for user interaction for receiving and storing data from the user, the data comprising a user-set tolerance; and
- wherein the display means displays the indicators so that they have a size which is proportional to the magnitude of the difference, and a color which is dependent upon the magnitude that the difference exceeds a percentage of the user-set tolerance stored in the data storage means.

28. Apparatus for monitoring and sensing changes in position of a patient from a prior position at a prior time to a current position at a current time, which apparatus comprises:
- a source of radiation for applying radiation to a patient;
- a plurality of targets adapted to be releasably affixed at both a current time and a prior time to the patient, for reflecting radiation impinging thereon;
- camera and computer means for detecting the reflected radiation from the targets and for determining current and prior positions of the targets in three-dimensional space, based on the target fixation at the current and prior times, respectively;
- data storage means for storing data representative of at least the prior position of the targets;
- computer means for comparing the current position of the targets with the stored prior position data for those targets, and developing from said comparing position signals representative of a difference in position of said patient from said prior time to said current time;
- user means for causing input to and storage by said data storage means of user-set tolerances; and
- display means responsive to said position signals for displaying indicators which are representative of said difference in position of said patient by causing the indicators to have a size which is proportional to the magnitude of the difference, and a color which is dependent upon the magnitude that the difference exceeds a percentage of the user-set tolerance stored in the data storage means.

29. The apparatus of claim 28 wherein the display means further comprises means for displaying an indicator in a first color if the difference exceeds a first limit and in a second color if the difference exceeds a second limit.

30. The apparatus of claim 28 wherein the display means further comprises means for displaying the differences in a predetermined color if the differences do not exceed the percentage of the user-set tolerance.

31. The apparatus of claim 29 wherein the first color is orange and the second color is red.

32. The apparatus of claim 29 wherein the first limit comprises a first percentage of the user-set tolerance and the second limit comprises a second percentage of the user-set tolerance.

33. The apparatus of claim 30 wherein the predetermined color is green.

34. Apparatus for monitoring and sensing changes in the position of a patient from a prior position at a prior time to a current position at a current time, which apparatus comprises:
   a source of radiation for directing a predetermined narrow spectral bandwidth of radiation towards a patient;
   a plurality of targets adapted to be releasably affixed at both a current time and a prior time to the patient, said targets having a reflecting surface thereon for reflecting the predetermined narrow spectral bandwidth of radiation directed to the patient and impinging thereon;
   camera means having an optical bandpass filter at its optical input which passes substantially only said predetermined narrow bandwidth, and which is directed to said targets for detecting the reflected radiation from the targets and providing at an output an image signal representative of said detection;
   position determining means coupled to said camera means and responsive to said image signal for determining current and prior positions of the targets in three-dimensional space, based on the target fixation at the current and prior times, respectively;
   data storage means for storing at least the prior position data of the targets;
   computer means for comparing the current position of individual ones of the uniquely identified targets with the prior position data stored in the data storage means for those targets, and developing from said comparing position signals representative of a difference in position of said patient from said prior time to said current time; and
   display means responsive to said position signals for displaying indicators which are representative of said difference in position of said patient.

35. The apparatus of claim 34, wherein said source of radiation comprises an infrared light source, and said optical filter comprises a infrared light filter.

36. A method for monitoring and sensing changes in the position of a patient from a prior time to a current time, said method comprising the following steps:
   applying a plurality of indicating marks to a surface portion of a patient whose position is to be monitored, said applying being done before the prior time;
   releasably affixing a plurality of individual radiation reflecting targets to the patient so that each target of said plurality is aligned with an indicating mark at the current time and prior time;
   directing radiation towards the patient;
   detecting radiation reflected from individual ones of the targets at the current time and prior times, uniquely identifying individual ones of said targets from which radiation was detected, and determining current and prior positions for individual ones of the uniquely identified targets in three-dimensional space, based on the target fixation at the current and prior times, respectively;
   storing data representative of at least the prior position of the targets;
   comparing the current position of the targets with the prior data stored for those identified targets, and developing from said comparing position signals representative of a difference in position of said patient from said prior time to said current time; and
   displaying said position signals as an indication of the difference in position of the patient from said prior time to said current time, thereby monitoring the position of the patient.

37. The method of claim 36, wherein:
   said displaying step comprises displaying indicators in a three-dimensional coordinate system, which indicators have a size which is proportional to the magnitude of the difference, and a color which is dependent upon the magnitude that the difference exceeds a percentage of the tolerance stored in the data storage means.

38. The method of claim 36, wherein said affixing step comprises:
   affixing individual radiation reflecting targets to the patient at the current time and prior time, each target comprising a body of substantially flat material having affixing means disposed on one side of the body for affixing the body to the patient, and retroreflecting means disposed on the other side of the body for retroreflecting radiation, the retroreflector means comprising a first portion which is retroreflective and a second portion which is not retroreflective and allows said indicating marks to be visible therethrough, so that during this affixing step said second portion of each of said targets is aligned with said indicating marks on said surface of said patient.

39. The method of claim 36, wherein:
   said comparing step comprises comparing a center of mass calculated for the current position of said targets to a center of mass calculated for the prior position of said targets.

40. The method of claim 36, wherein said detecting step comprises:
   calculating position vectors between each one of a plurality of said target, and a relative angular relationship between each one of said vectors at both of the current and prior times, and comparing the calculated vectors and their relative angular relationship at said current time to the calculated vectors and their angular relationship at said prior time, for uniquely identifying a plurality of said targets and their current position, and therefor said patient, in three-dimensional space.

41. The method of claim 40, wherein:
   said comparing step comprises individually comparing the current position of individual ones of said uniquely identified targets to the prior position of those identified targets; and
   said displaying step comprises displaying magnitudes in a three-dimensional coordinate system, said magnitudes being representative of the difference between the current three-dimensional position and a prior three-dimensional position of the patient, thereby monitoring the position of the patient.

* * * * *